United States Patent [19]
Miller et al.

[11] Patent Number: 5,874,657
[45] Date of Patent: Feb. 23, 1999

[54] PROCESS FOR THE PURIFICATION OF 1,1-DIFLUOROETHANE

[75] Inventors: Ralph Newton Miller, Newark, Del.; Barry Asher Mahler, Glen Mills, Pa.

[73] Assignee: E. I. du Pont de Nemours and Company, Wilmington, Del.

Related U.S. Application Data

[60] Provisional application No. 60/030,148 Nov. 1, 1996.

[21] Appl. No.: 959,869

[22] Filed: Oct. 29, 1997

[51] Int. Cl.⁶ .................................................. C07C 17/38
[52] U.S. Cl. ............................................ 570/178; 570/180
[58] Field of Search ...................................... 570/178, 180

[56] References Cited

U.S. PATENT DOCUMENTS

| | | | |
|---|---|---|---|
| 5,001,287 | 3/1991 | Fernandez et al. | 570/178 |
| 5,095,158 | 3/1992 | Bolmer | 570/180 |
| 5,200,431 | 4/1993 | Dattani et al. | 570/178 |
| 5,306,850 | 4/1994 | Darago | 570/178 |

*Primary Examiner*—Alan Siegel
*Attorney, Agent, or Firm*—James E. Shipley

[57] ABSTRACT

The present invention relates to processes for separating 1,1-difluoroethane (HFC-152a) from vinyl chloride by using extractive distillation with an extractive agent selected from the aliphatic hydrocarbons, chlorocarbons and alcohols.

9 Claims, 1 Drawing Sheet

PROCESS FOR THE PURIFICATION OF 1,1-DIFLUOROETHANE

CROSS REFERENCE TO RELATED APPLICATIONS

This application claims the priority benefit of U.S. Provisional Application 60/030,148, filed Nov. 1, 1996 now abandoned.

FIELD OF THE INVENTION

The present invention relates to processes for separating vinyl chloride and other compounds from 1,1-difluoroethane by using extractive distillation employing aliphatic hydrocarbons, chlorocarbons, and alcohols.

BACKGROUND OF THE INVENTION

New regulations have been established to protect the stratospheric ozone layer from possible damage by fully halogenated chlorofluorocarbons (CFCs). 1,1-Difluoroethane ($CHF_2CH_3$ or HFC-152a) is a non-chlorine containing fluorocarbon that is especially valuable as a refrigerant, blowing agent, propellant, and chemical intermediate for manufacture of vinyl fluoride, among other uses.

1,1-Difluoroethane may be prepared by reacting vinyl chloride with hydrogen fluoride in the presence of a catalyst such as a palladium, vanadium, tin, or other catalysts. The reaction product from such processes typically contains, in addition to the desired 1,1-difluoroethane, unreacted vinyl chloride and hydrogen fluoride, by-product hydrogen chloride and small amounts of organic by-products such as 1-chloro-1-fluoroethane and vinyl fluoride. While the majority of these impurities can be removed by conventional distillation, vinyl chloride is very difficult to separate from 1,1-difluoroethane when the 1,1-difluoroethane concentration is above about 85 mole %. Depending on the temperature, vinyl chloride and 1,1-difluoroethane in these concentrations form either an azeotrope or azeotrope-like composition, making purification of 1,1-difluoroethane by conventional distillation difficult or impossible.

The presence of even relatively small amounts of vinyl chloride in the 1,1-difluoroethane product is undesirable in many applications of this product. Numerous attempts have been made to reduce the amount of vinyl chloride remaining in the 1,1-difluoroethane but these have been inadequate for achieving low levels of vinyl chloride or have been costly to operate.

The present invention solves problems associated with conventional purification methods by providing processes for removing 1,1-difluoroethane from mixtures comprising 1,1-difluoroethane and vinyl chloride which is simple and effective for obtaining low levels of vinyl chloride in the 1,1-difluoroethane product.

SUMMARY OF THE INVENTION

A process has been discovered for separating 1,1-difluoroethane from a first mixture comprising 1,1-difluoroethane and vinyl chloride, comprising the steps of:

contacting the first mixture with at least one extractive agent selected from the group consisting of hydrocarbons, alcohols, and chlorocarbons having a normal boiling point greater than about 10° C. and less than about 120° C. to form a second mixture, and separating 1,1-difluoroethane from the vinyl chloride of the second mixture by extractively distilling the second mixture, thereby recovering 1,1-difluoroethane substantially free of vinyl chloride.

Figure 1:
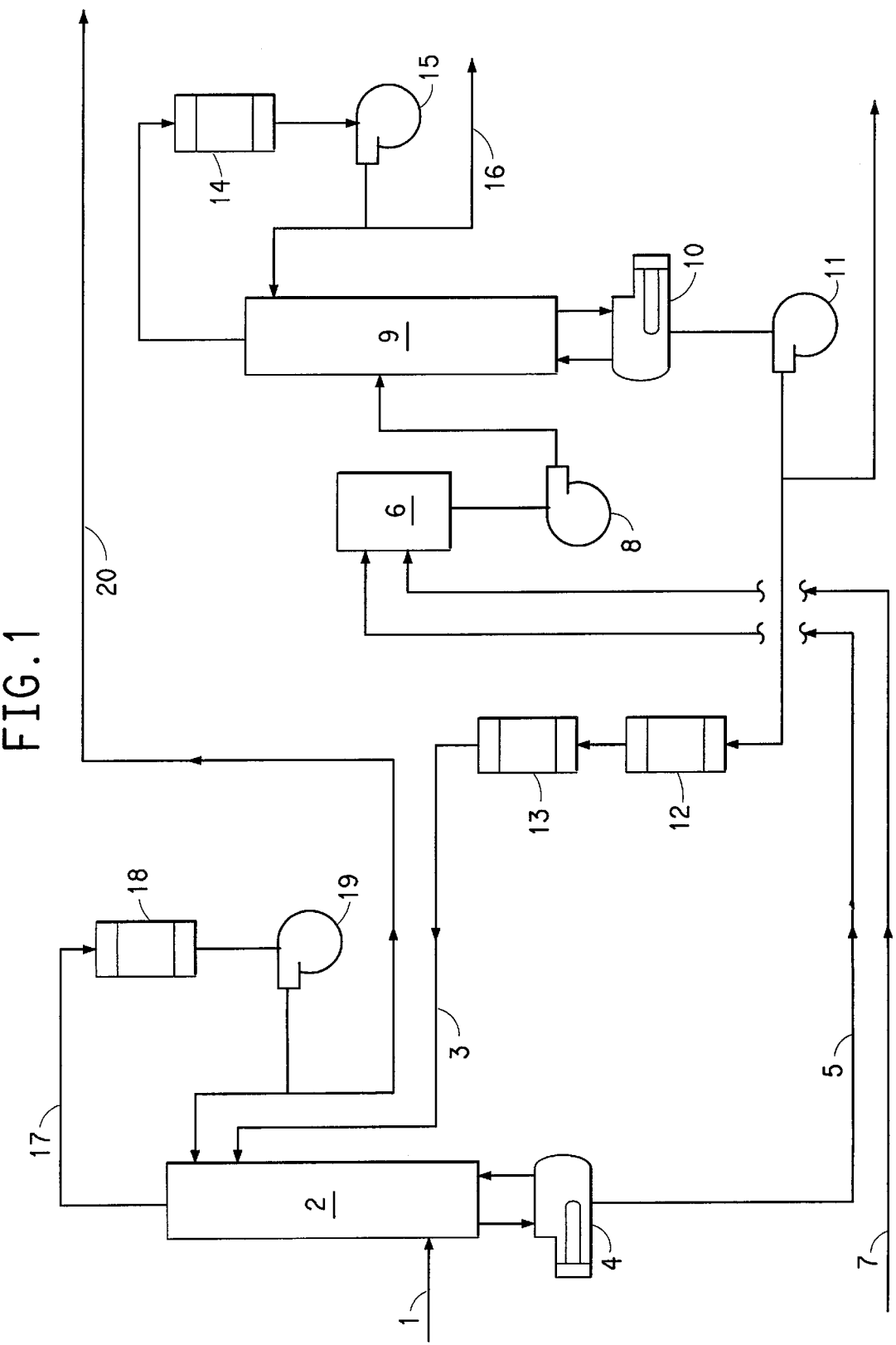
FIG. 1—FIG. 1 is a schematic diagram of an extractive distillation system that can be used for practicing an aspect of the inventive process.

DETAILED DESCRIPTION 1,1-Difluoroethane (HFC-152a) is typically made by fluorination of vinyl chloride monomer (VCM) by using hydrogen fluoride in the presence of a catalyst. The 1,1-difluoroethane product may contain a variety of impurities such as by-product hydrogen chloride, co-products such as 1-chloro-1-fluoroethane, 1,1-dichloroethane, and vinyl fluoride, as well as unreacted vinyl chloride, and hydrogen fluoride, among others. While most of these impurities can be removed from 1,1-difluoroethane by conventional distillation, small amounts of vinyl chloride are difficult, if not impossible, to remove by using conventional distillation methods because of azeotrope or pinchpoint formation between 1,1-difluoroethane and vinyl chloride. The term "conventional distillation" refers to the practice where only the relative volatilities of the components of a mixture to be separated are used to separate the components.

To determine the relative volatility of 1,1-difluoroethane and vinyl chloride, a method known in this field as the PTx method was used. In the PTx method, the total absolute pressure in a cell of known volume is measured at a constant temperature for various known binary compositions of 1,1-difluoroethane and vinyl chloride. Use of the PTx method is described in detail in "Phase Equilibrium in Process Design," Wiley-Interscience Publisher, 1970, written by Harold R. Null, pages 124 through 126; the entire disclosure of which is hereby incorporated by reference. These total pressure measurements are converted into equilibrium vapor and liquid compositions in the cell by employing an activity coefficient equation model such as the Non-Random, Two Liquid (NRTL) equation, which represents liquid phase non-idealities. Use of an activity coefficient equation such as the NRTL equation, is described in greater detail in "The Properties of Gases and Liquids," $4^{th}$ edition, published by McGraw Hill, written by Reid, Prausnitz and Poling, pages 241 through 387; and in "Phase Equilibria in Chemical Engineering," published in 1985 by Butterworth Publishers, written by Stanley M. Walas, pages 165 through 244. The entire disclosure of each of the previously identified references is hereby incorporated by reference. Without wishing to be bound by any theory or explanation, it is believed that the NRTL equation can sufficiently predict whether or not mixtures comprising 1,1-difluoroethane and vinyl chloride behave in an ideal manner, and can sufficiently predict the relative volatilities of the components in such mixtures.

The results of the PTx measurements and the above series of calculations indicate that the relative volatilities of 1,1-difluoroethane and vinyl chloride are equal to about 1.0 for given compositions of 1,1-difluoroethane and vinyl chloride over a range of temperatures. Relative volatilities of about 1.0 in a mixture indicate the formation of an azeotrope. The results of PTx measurements and the above calculations indicate that the composition of the azeotrope varies with temperature. Table 1 shows the results of these calculations; specifically how the composition of the azeotrope formed varies over the range of temperatures. Because of the formation of an azeotrope, it is difficult, if not impossible, to completely separate 1,1-difluoroethane and vinyl chloride by conventional distillation at temperatures and pressures within the ranges shown in Table 1.

TABLE 1

Variation of 1,1-Difluoroethane/Vinyl Chloride Azeotrope Composition with Temperature

| Temp. °C. | VCM Mole Fraction | HFC-152a Mole Fraction | Pressure psia |
|---|---|---|---|
| −80.0 | 0.18680 | 0.81320 | 0.55 |
| −60.0 | 0.16112 | 0.83888 | 2.24 |
| −40.0 | 0.13250 | 0.86750 | 6.93 |
| −20.0 | 0.10120 | 0.89880 | 17.59 |
| 0.0 | 0.06771 | 0.93229 | 38.32 |
| 10.0 | 0.05050 | 0.94950 | 54.05 |
| 20.0 | 0.03320 | 0.96680 | 74.31 |
| 30.0 | 0.01610 | 0.98390 | 99.92 |
| 35.0 | 0.00790 | 0.99210 | 114.98 |
| 39.0 | 0.00150 | 0.99850 | 128.22 |
| 39.9 | 0.00005 | 0.99995 | 131.33 |

Based on the PTx cell measurements and calculations, the azeotrope disappears above a temperature of about 39.9° C. to 40.0° C. However, above this temperature the relative volatilities of 1,1-difluoroethane and vinyl chloride still approach a value of 1.0, indicative of a vapor-liquid equilibrium pinch-point, which, in turn, indicates that it is still essentially impossible to separate the components by conventional distillation.

Within the temperature and pressure range shown in Table 1, obtaining pure 1,1-difluoroethane from a mixture with vinyl chloride would require starting with a composition purer than the azeotrope, and the remainder of the 1,1-difluoroethane would necessarily end up as the azeotrope. Distillation at a temperature below −80° C. and a pressure below 0.55 psia would require a very low temperature vacuum distillation. Consequently, using conventional distillation to obtain high purity HFC- 152a would be costly and require a very large column.

By "azeotrope" or "azeotropic" composition is meant a constant boiling liquid mixture of two or more substances that behaves as a single substance. One way to characterize an azeotropic composition or mixture is that the vapor produced by partial evaporation or distillation of the liquid has the same composition as the liquid from which it was evaporated or distilled, e.g., the mixture distills/refluxes without compositional change. Constant boiling compositions are characterized as azeotropic because they exhibit either a maximum or minimum boiling point, as compared with that of the non-azeotropic mixtures of the same components. An azeotropic composition can also be characterized as the maximum or minimum vapor pressure for a mixture at a given temperature when plotted as a function of mole fraction.

By "azeotrope-like" is meant a composition that has a constant boiling characteristic or a tendency not to fractionate upon boiling or evaporation. The composition of the vapor formed is the same as, or substantially the same as, the original liquid composition. During boiling or evaporation, the liquid composition, if it changes at all, changes only to a minimal or negligible extent. An azeotrope-like composition can also be characterized by the area that is adjacent to the maximum or minimum vapor pressure. This can be seen by plotting vapor pressure at a given temperature as a function of mole fraction. It is recognized in the art that a composition is azeotrope-like if, after about 50 weight percent of the composition is removed such as by evaporation or boiling off, the difference between the original composition and the composition remaining is less than about 6%, and normally less than about 3%, relative to the original composition.

1,1-Difluoroethane and vinyl chloride can be partialy purified by using the aforementioned azeotropic and azeotrope-like compositions in a process that comprises forming these low-boiling, high pressure azeotropes or azeotrope-like compositions within a conventional distillation column. For example, the conventional distillation column can be operated at a temperature and pressure that causes an azeotropic or azeotrope-like composition to form. If the quantity of 1,1-difluoroethane is relatively large in comparison to the vinyl chloride, i.e., the concentration of 1,1-difluoroethane is greater than that in the azeotropic or azeotrope-like composition, the 1,1-difluoroethane can be removed in substantially pure form from the bottom of the column, while the azeotropic or azeotrope-like composition is removed from the top of the column. Conversely, if the quantity of vinyl chloride is relatively large in comparison to the 1,1-difluoroethane, i.e., the concentration of vinyl chloride is greater than that in the azeotropic or azeotrope-like composition, the vinyl chloride can be removed in substantially pure form from the bottom of the column, while the azeotropic or azeotrope-like composition is removed from the top of the column.

The results of PTx cell measurements and the previous calculations for 1,1-difluoroethane and vinyl chloride with various proposed extractive agents are summarized below in Table 2. Table 2 gives activity coefficients of 1,1-difluoroethane (HFC-152a) and vinyl chloride (VCM) at infinite dilution in the listed extraction agent, and also gives the ratios of HFC-152a/VCM activity coefficients (relative volatility) at 0° C. (except as noted in Table 2). The ratio of the activity coefficient of the 1,1-difluoroethane at infinite dilution in the proposed extractive agent relative to the activity coefficient of the vinyl chloride at infinite dilution in the proposed extractive agent is considered to be the relative volatility of the 1,1-difluoroethane to the vinyl chloride in the presence of the proposed extractive agent. "NBP" is the boiling point of the compound at atmospheric pressure.

TABLE 2

Proposed Extractive Agents for HFC-152a/VCM

| | | | Infinite Dilution Activity Coefficients at 0° C. | | |
|---|---|---|---|---|---|
| | Formula | NBP (C) | HFC-152a | VCM | Ratio |
| Extractive Agent | | | | | |
| chloroethane | $CH_2ClCH_3$ | 12.3 | 1.62 | 1.02 | 1.59 |
| n-Pentane | $C_5H_{12}$ | 36.1 | 5.03* | 1.40 | 3.59 |
| methylene chloride | $CH_2Cl_2$ | 39.8 | 2.09 | 1.34 | 1.56 |
| cyclopentane | $C_5H_{10}$ | 49.3 | 4.53 | 1.52 | 2.98 |
| 1,1-dichloroethane | $CHCl_2CH_3$ | 57.3 | 1.81 | 1.07 | 1.69 |
| chloroform | $CHCl3$ | 61.2 | 2.28 | 1.00 | 2.28 |
| methanol | $CH_3OH$ | 64.6 | 4.82 | 3.71 | 1.30 |
| n-hexane | $C_6H_{14}$ | 68.7 | 5.35 | 1.47* | 3.64 |
| carbon tetrachloride | $CCl_4$ | 76.6 | 4.67 | 1.27 | 3.68 |
| ethanol | $C_2H_5OH$ | 78.3 | 5.37 | 2.97 | 1.81 |
| cyclohexane | $C_6H_{12}$ | 80.7 | 6.65 | 1.48 | 4.49** |
| 1,2-dichloroethane | $CH_2ClCH_2Cl$ | 83.4 | 2.41 | 1.34* | 1.80 |
| propanol | $C_3H_7OH$ | 97.1 | 5.85 | 2.54 | 2.30 |
| n-heptane | $C_7H_{16}$ | 98.4 | 4.77 | 1.27 | 3.76 |
| 1,1,2-trichloroethane | $CHCl_2CH_2Cl$ | 113.9 | 2.65 | 1.22* | 2.17 |
| Not Viable Extractive Agents | | | | | |
| HCFC-151a | $CHClFCH_3$ | 16.2 | 1.14 | 1.07 | 1.07 |
| HCFC-123 | $CHCl_2CF_3$ | 27.8 | 1.03 | 0.98 | 1.05 |
| acetone | $CH_3COCH_3$ | 56.3 | 1.02 | 0.99 | 1.03 |

Notes:
*Literature data
**These data are for 25° C. (The melting point of cyclohexane is +6.5° C., so the extraction column could not be operated at 0° C.)

The problems associated with conventional distillation can be solved by an extractive distillation process. Extractive distillation may be employed when the components of the mixture have relative volatilities that are insufficient to permit effective separation of the components by conventional distillation. In extractive distillation, an extractive agent is added which causes the relative volatilities of the components of a mixture to be altered such that the relative volatility becomes sufficient to permit separation of the components. The difficulty in applying this method is that there is no known way of predicting which, if any, compound will be an effective extractive distillation agent.

Extractive distillation is typically performed by operating a continuous distillation column, which comprises a multistage distillation column with a minimum of two feed points, e.g., introducing the extractive agent at a first feed point which is located above a second feed point that is used for introducing the mixture to be separated, a reboiler, and an overhead condenser for returning reflux to the column. Other similar commercially available apparatus may also be employed.

The present inventors have discovered that vinyl chloride can be efficiently separated from 1,1-difluoroethane by using an extractive distillation process with an extractive agent selected from the group consisting of aliphatic hydrocarbons, chlorocarbons, and alcohols having a normal boiling point greater than about 10° C. and less than about 120° C. Preferred are agents with a normal boiling point between about 60° C. and 100° C. Examples of suitable extractive agents for the present process are normal pentane, cyclopentane, normal hexane, cyclohexane, normal heptane, chloromethane, dichloromethane (methylene chloride), trichloromethane (chloroform), carbon tetrachloride, chloroethane, 1,1-dichloroethane, 1,2-dichloroethane, 1,1,2-trichloroethane, methanol, ethanol, and propanol. The extractive agents used in the present invention are generally commercially available.

The extractive distillation process of the present invention for separating 1,1-difluoroethane from a first mixture comprising 1,1-difluoroethane and vinyl chloride comprises the steps of:

contacting the first mixture with an extractive agent selected from the group consisting of aliphatic hydrocarbons, chlorocarbons and alcohols having a normal boiling point greater than about 10° C. and less than about 120° C. to form a second mixture, and separating the 1,1-difluoroethane from the vinyl chloride of the second mixture by extractively distilling the second mixture in an extractive distillation zone thereby recovering 1,1-difluoroethane substantially free of vinyl chloride as an overhead product and from the bottom of the zone a third mixture comprising the extractive agent and vinyl chloride, and optionally separating the extractive agent from the third mixture.

By "substantially free" or "substantially pure," it is meant that the 1,1-difluoroethane contains less than about 1.0 weight % (wt %) of vinyl chloride, normally less than about 0.1 wt % of vinyl chloride, and in some cases less than about 10 parts per million (ppm) by weight of vinyl chloride.

The first mixture can be obtained from any suitable manufacturing process or source which produces 1,1-difluoroethane with vinyl chloride as an impurity: typically by reacting vinyl chloride with anhydrous hydrogen fluoride in the presence of metallic catalyst. Examples of the metallic catalyst which may be employed include palladium, vanadium, and tin compounds, among others. While the present invention is adaptable to a wide range of 1,1-difluoroethane/vinyl chloride compositions, it is preferred that the 1,1-difluoroethane content be greater than about 85 mole % and that the vinyl chloride content be less than about 15 mole %. If desired, conventional distillation can be used to reduce the initial quantity of vinyl chloride or other such impurities. That is, conventional distillation can be used for removing relatively large or bulk quantities of impurities from the first mixture which in turn is processed in accordance with the present inventive process for separating vinyl chloride and 1,1-difluoroethane.

The present invention is carried out in such a manner that the relative volatility of the 1,1-difluoroethane to the vinyl chloride is enhanced, with the 1,1-difluoroethane more volatile, and thus permitting 1,1-difluoroethane to be removed from the top of a distillation zone. Normally, the removed or recovered 1,1-difluoroethane is substantially free of vinyl chloride.

If desired, the extractive agents may be subsequently removed from the vinyl chloride impurity or impurity mixture by conventional distillation methods. The extractive agent can be recycled to the extractive distillation column for removing additional quantities of vinyl chloride from 1,1-difluoroethane.

In one aspect of the invention, an extractive agent is introduced at an upper feed point of an extractive distillation column, whereas the first mixture requiring separation is introduced at a relatively lower point in the column. The extractive agent passes downwardly through trays which are located in the center of the column and contacts the first mixture thereby forming a second mixture. While in the presence of the extractive agent, 1,1-difluoroethane is relatively more volatile than vinyl chloride, thereby allowing 1,1-difluoroethane to exit the top of the column. The 1,1-difluoroethane, which is exiting the top of the column, can be condensed by using conventional reflux condensers. At least a portion of this condensed stream can be returned to the top of the column as reflux, and the remainder recovered as a useful product, i.e., substantially pure 1,1-difluoroethane. If desired, the 1,1-difluoroethane can be transported to a second extractive distillation column and/or a second conventional distillation column for further purification.

Vinyl chloride, extractive agent and possibly other impurities comprise a third mixture that exits from the bottom of the column, which can in turn then be passed to a stripper or conventional distillation column for separation by using conventional distillation or other known methods. If desired, the extractive agent may then be recycled to the extractive distillation column. In some cases, the vinyl chloride, after removal of the extractive agent by conventional distillation, is recovered as a useful product for sale or other use, e.g., manufacture of 1,1-difluoroethane. The recovered vinyl chloride can also be transported to a second or third conventional and/or extractive distillation column for removing other impurities, thereby obtaining substantially pure vinyl chloride for sale or other use.

If a water soluble extractive agent such as ethanol or other alcohol is employed, the extractive agent can optionally be removed from vinyl chloride by other methods such as water extraction. For example, a mixture of vinyl chloride and water soluble extractive agent is passed through water whereby the alcohol is preferentially extracted.

The ratio of the material exiting the top of the extractive distillation column, which is then condensed and in turn returned to the column, to the amount of material that is removed as product is commonly referred to as the reflux ratio. The reflux ratio will define the physical characteristics of the extractive distillation column.

In general, an increase in the reflux ratio will in turn cause an increase in the purity of the overhead 1,1-difluoroethane by reducing or eliminating the quantity of extractant or other impurities in the overhead 1,1-difluoroethane.

The specific conditions that can be used for practicing the process of the present invention are not critical and depend upon a number of interrelated design parameters such as the diameter of the column, selected feed points, the number of separation stages in the column, among other parameters. The operating pressure of the distillation system may range from about 15 to about 350 psia, normally about 50 to 300 psia. The temperature and heat transfer area of the overhead condenser is normally sufficient to substantially fully condense the overhead product, or is optionally sufficient to achieve the desired reflux ratio by partial condensation.

The effective amount of the extractive agent can vary widely. In general, using an increased amount of extractive agent will enhance the purity of the overhead 1,1-difluoroethane. Typically, the ratio of extractive agent to 1,1-difluoroethane ranges from about 1/1 to about 10/1 on a weight basis; however, higher ratios can be employed as needed.

The temperature that is employed at a given step in the inventive process is a function of the pressure and the design characteristics of the distillation column, e.g., the ratio of extractive agent to the first mixture.

Certain aspects of the invention can be better understood by reference to FIG. 1. FIG. 1 schematically illustrates a system which can be used for performing one aspect of the present extractive distillation process. A first mixture comprising 1,1-difluoroethane with vinyl chloride as impurity is supplied via conduit 1 to extraction column 2. At least one liquid extractive agent is supplied via conduit 3 to the extraction column 2, and introduced into column 3 at a location above the mixture 1. A second mixture comprising the extractive agent(s) and vinyl chloride is removed from the bottom of column 2 and transported to steam-heated reboiler 4. In some cases, the reboiler 4 is attached to the extractive column 2. The second mixture is supplied via conduit 5 to a feed tank 6. Supplemental liquid extractive agent is also supplied to feed tank 6 via conduit 7 thereby forming a third mixture or extractive agent recycle. A pump 8 transports the third mixture to a stripping mixture column 9. Stripping column 9 separates the extractive agents from nonextractive agents. Extractive agent is removed from column 9 and supplied to a second steam heated reboiler 10. In some cases, the reboiler 10 is attached to column 9. Pump 11 transports the extractive agent from the reboiler 10 through a cold water chiller 12, and then to chiller 13. If necessary, excess quantities of extractive agent can be purged prior to reaching chiller 12. Typically, chiller 13 is operated at a temperature of about −25° C. After exiting chiller 13, the extraction agent is supplied via conduit 3 into extraction column 2.

Vinyl chloride can exit from the top of stripping column 9 as an off gas, and is introduced into condenser 14, which is typically operated at a temperature of about −25° C. While under reflux conditions, pump 15 returns a portion of the vinyl chloride to the stripping column 9. The remaining portion of the vinyl chloride can be removed from the system via conduit 16.

An off gas can also removed from extraction column 2. The off gas can be 1,1-difluoroethane that is substantially free of vinyl chloride and other fluorocarbons. The 1,1-difluoroethane is transported via conduit 17 to condenser 18. Condenser 18 is typically operated at a temperature of about −25° C. While under reflux conditions, pump 19 returns a portion of the 1,1-difluoroethane to extraction column 2. The 1,1-difluoroethane can be removed from the system via conduit 20.

In order for the extractive agent to be most effective for enhancing the volatility of the 1,1-difluoroethane, the relative volatility of the 1,1-difluoroethane to the vinyl chloride in the presence of the extractive agent must theoretically be greater than about 1.0; for practical purposes it must generally be greater than about 1.1. Normally, this relative volatility will be greater than about 1.5, and still more preferably it will be above about 2.0.

EXAMPLES

The following Examples are provided to illustrate certain aspects of the present invention, and do not limit the scope of the invention as defined by the appended claims. The following Examples employ the NRTL interaction parameters identified above. In the following Examples, each stage is based upon a 100% operational or performance efficiency. Differing column designs and operating conditions are employed using different extractive agents in order to maximize the performance of each distillation. In all examples, the total theoretical stages includes condenser and reboiler, with the condenser counted as stage No. 1.

Comparative Example 1

In this example, a distillation column with 100 theoretical stages is used for purifiing a feed stream composed of 1000 lb/hr of crude HFC-152a containing 0.1 lb/hr of VCM, a VCM concentration of 100 ppm. No other impurities are in the feed. The feed is introduced on stage 50, with the column condenser pressure at 37.7 psia. The distillate temperature is about 0° C., and the bottom column temperature is about 1.8° C. Under these operating conditions, the HFC-152a product will leave in the bottoms stream from the column. The column reflux rate is set so as to meet a composition of 10 ppm of VCM in the HFC-152a bottoms product. The column diameter is chosen so as to have a maximum F-factor (a standard measure of allowable flow volume rates per unit of column cross-sectional area) of 1.3 or below. In this example, the column diameter is 40 inches and the F-factor is 1.12. The results of using this distillation process are shown below in Table 3.

TABLE 3

Removal of VCM from HFC-152a using Distillation (37.7 psia)

| Distillate | | | | | | | 152a |
|---|---|---|---|---|---|---|---|
| Reflx. | | | | | Tails | | |
| Flow lb/hr | VCM lb/hr | 152a lb/hr | Temp (C.) | 152a lb/hr | VCM PPM | Temp (C.) | Recov. % |
| 25000 | 0.9 | 183 | 0 | 817 | 10 | 1.8 | 81.7 |

Comparative Example 2

This test is carried out under the same conditions as Comparative Example 1 except that the column pressure is 14.7 psia, the distillate temperature is about −24° C., and the bottom column temperature is about −19.7° C. In this example, the column diameter is 28 inches and the F-factor is 1.10. The results of this distillation process are shown below in Table 4.

TABLE 4

Removal of VCM from HFC-152a using Distillation (14.7 psia)

| Reflx. | | | | Tails | | | 152a |
|---|---|---|---|---|---|---|---|
| Flow lb/hr | VCM lb/hr | 152a lb/hr | Temp (C.) | 152a lb/hr | VCM PPM | Temp (C.) | Recov. % |
| 7500 | 0.9 | 204 | −24 | 796 | 10 | −19.7 | 79.6 |

Comparative Example 3

This test is carried out under the same conditions as Comparative Example 1 except that the column pressure is 4.05 psia, the distillate temperature is about −49.7° C., and the bottom column temperature is about −39.5° C. In this example, the column diameter is 24 inches and the F-factor is 1.19. The results of this distillation process are shown below in Table 5.

TABLE 5

Removal of VCM from HFC-152a using Distillation (4.05 psia)

| Reflx. | | | | Tails | | | 152a |
|---|---|---|---|---|---|---|---|
| Flow lb/hr | VCM lb/hr | 152a lb/hr | Temp (C.) | 152a lb/hr | VCM PPM | Temp (C.) | Recov. % |
| 3000 | 0.9 | 384 | −49.7 | 616 | 10 | −39.5 | 61.6 |

The above Comparative Examples 1,2 and 3 show that conventional distillation is relatively ineffective for separating VCM from HFC-152a, with a very low recovery of HFC-152a. However, these examples do show how the concentration of VCM can be reduced from a mixture comprising VCM and HFC-152a by azeotropic distillation

Example 1

In this Example of the invention, an extractive distillation column with 37 theoretical stages is used for purifiing a feed stream composed of 1000 lb/hr of crude HFC-152a containing 0.1 lb/hr of VCM, a VCM concentration of 100 part per million (ppm). No other impurities are in the feed. The feed is introduced on stage 25 and n-hexane extractive agent on stage 10, with the column condenser pressure at 34.7 psia. The distillate temperature is −2.7° C., and the bottom column temperature is 100.0° C. Under these operating conditions, the HFC-152a product will leave in the overhead stream from the column. The VCM and n-hexane will exit in the bottom stream. The extractive agent flow rate is set so as to meet a composition of 1 ppm of VCM in the HFC-152a overhead product. The column reflux rate is set so as to meet a composition of 10 ppm of extractive agent in the HFC-152a overhead product. The distillate rate is controlled to recover 998.0 lb/hr of HFC-152a in the distillate overhead stream. The column diameter is chosen so as to have an F-factor of 1.3 or below. In this example, the F-factor is 1.12. The results of using this inventive extractive distillation process are shown below in Table 6.

TABLE 6

Removal of VCM from HFC-152a using n-Hexane as Extractive Agent

| Extr. Flow | Reflx. | | | | | Tails | | | 152a |
|---|---|---|---|---|---|---|---|---|---|
| Recov. lb/hr | Flow lb/hr | VCM ppm | 152a lb/hr | Extr. ppm | Temp (C.) | Extr. lb/hr | 152a lb/hr | VCM lb/hr | Temp (C.) | Recov. % |
| 1488 | 1311 | 1 | 998 | 10 | −2.7 | 1488 | 1.9 | 0.1 | 100.0 | 99.8 |

Example 2

In this series of tests, conditions are the same as in Example 1 except as noted. Table 7 below summarizes extractive distillations using n-hexane and other hydrocarbon extractive agents useful in the inventive process. In each of the cases in Table 7, the overall recovery of HFC-152a is 99.8%, and the concentrations of VCM and extractive agent in the HFC-152a product are 1 and 10 ppm by weight respectively. Column geometry, extractive agent flow and reflux flow are varied to achieve these results.

TABLE 7

Removal of VCM from HFC-152a using Hydrocarbons as Extractive Agents

| | Cyclo-Hexane | Pentane | n-Hexane | n-Heptane | Cyclo-Pentane |
|---|---|---|---|---|---|
| Column Design: | | | | | |
| No. of Theor. Stages | 62 | 37 | 32 | 39 | 32 |
| HFC-152a Feed Stage | 50 | 25 | 20 | 27 | 20 |
| Extractive Agent Feed Stage | 35 | 9 | 5 | 15 | 9 |
| Column Diameter (Inches) | 18 | 12 | 14 | 14 | 12 |
| Distillate Temp (°C.) | −2.7 | −2.7 | −2.7 | −2.7 | 20.2 |
| Bottoms Temp (°C.) | 66.1 | 100.0 | 130.4 | 79.9 | 145.5 |
| Operating Pres (psia) | 34.7 | 34.7 | 34.7 | 34.7 | 74.7 |
| Flowrates (lb/hr): | | | | | |
| Feed | 1000 | 1000 | 1000 | 1000 | 1000 |
| Extractive Agent | 1587 | 1488 | 1620 | 1594 | 1702 |
| Reflux | 3823 | 1311 | 1230 | 1857 | 2207 |
| Maximum F-factor | 1.17 | 1.3 | 0.93 | 1.16 | 1.16 |
| HFC-152a Recovery (%) | 99.8 | 99.8 | 99.8 | 99.8 | 99.8 |
| HFC-152a Purity (wt %) | 99.999 | 99.999 | 99.999 | 99.999 | 99.999 |

Example 3

The conditions, flowrates and HFC-152a purity in this example are the same as in Example 1 except as modified for the use of certain alcohols as extractive agents. The column design was modified as shown in the summary in Table 8.

TABLE 8

Removal of VCM from HFC-152a using Alcohols as Extractive Agents

| | Methanol | Ethanol | Propanol |
|---|---|---|---|
| Column Design: | | | |
| No. Of Theor. Stages | 57 | 38 | 32 |
| HFC-152a Feed Stage | 45 | 26 | 20 |
| Extractive Agent Feed Stage | 10 | 6 | 4 |
| Column Diameter (Inches) | 16 | 14 | 14 |
| Distillate Temp (°C.) | −2.7 | −2.7 | −2.7 |
| Bottoms Temp (°C.) | 90.4 | 103.9 | 123.7 |
| Operating Pres (psia) | 34.7 | 34.7 | 34.7 |

TABLE 8-continued

Removal of VCM from HFC-152a using Alcohols as Extractive Agents

| | Methanol | Ethanol | Propanol |
|---|---|---|---|
| Flowrates (Lb/Hr): | | | |
| Feed | 1000 | 1000 | 1000 |
| Extractive Agent | 5937 | 4245 | 3459 |
| Reflux | 1689 | 1021 | 1056 |
| Maximum F-factor | 1.18 | 1.14 | 0.97 |
| HFC-152a Recovery (%) | 99.8 | 99.8 | 99.8 |
| HFC-152a Purity (wt %) | 99.999 | 99.999 | 99.999 |

Example 4

The conditions, flowrates and HFC-152a purity in this example are the same as in Example 1 except as modified for the use of certain chlorocarbons as extractive agents. The column design was modified as shown in the summary in Table 9.

TABLE 9

Removal of VCM from HFC-152a Using Chlorocarbons as Extractive Agents

| | HCC-160 | HCC-30 | HCC-20 | CC-10 | HCC-150 | HCC-140 |
|---|---|---|---|---|---|---|
| Column Design: | | | | | | |
| No. of Theor. Stages | 63 | 57 | 45 | 39 | 47 | 37 |
| HFC-152a Feed Stage | 45 | 45 | 33 | 27 | 35 | 25 |
| Extractive Agent Feed Stage | 17 | 10 | 7 | 7 | 5 | 4 |
| Column Diameter (Inches) | 18 | 16 | 12 | 14 | 16 | 16 |
| Distillate Temp (°C.) | −2.7 | −2.7 | −2.7 | −2.7 | −2.7 | −2.7 |
| Bottoms Temp (°C.) | 39.9 | 69.0 | 92.2 | 109.0 | 116.7 | 149.2 |
| Operating Pres (psia) | 34.7 | 34.7 | 34.7 | 34.7 | 34.7 | 34.7 |
| Flowrates (lh/hr): | | | | | | |
| Feed | 1000 | 1000 | 1000 | 1000 | 1000 | 1000 |
| Extractive Agent | 1895 | 6795 | 3494 | 2791 | 4156 | 5320 |
| Reflux | 3686 | 1379 | 1134 | 1013 | 998 | 802 |
| Maximum F-factor | 1.11 | 1.15 | 1.19 | 1.02 | 1.07 | 1.26 |

TABLE 9-continued

Removal of VCM from HFC-152a Using Chlorocarbons as Extractive Agents

|  | HCC-160 | HCC-30 | HCC-20 | CC-10 | HCC-150 | HCC-140 |
|---|---|---|---|---|---|---|
| HFC-152a Recovery (%) | 99.8 | 99.8 | 99.8 | 99.8 | 99.8 | 99.8 |
| HFC-152a Purity (wt %) | 99.999 | 99.999 | 99.999 | 99.999 | 99.999 | 99.999 |

*The identities of the above chlorocarbons is as follows: HCC-160 (chloroethane), HCC-30 (methylene chloride), HCC-20 (chloromethane), CC-10 (carbon tetrachloride), HCC-150 (1,2-dichloroethane), and HCC-140 (1,1,2-trichloroethane).

Given the existence of azeotropes at mole fractions of 1,1-difluoroethane greater than about 81% in a mixture with vinyl chloride (Table 1), it is a surprising and an unexpected result that vinyl chloride can be separated from 1,1-difluoroethane to yield a substantially pure 1,1-difluoroethane by extractive distillation using certain readily available and low cost fluorine-free compounds. Other extraction agents that may also be used for the purification of 1,1-difluoroethane by the removal of vinyl chloride include: aliphatic hydrocarbons, chlorocarbons and/or alcohols having a normal boiling point greater than about 10° C. and less than about 120° C.

For each of the three classes of extractive agents (hydrocarbons, alcohols, chlorocarbons), the required extractive agent flow and the number of stages decreases as the activity coefficient ratio increases (i.e., larger ratios are better). While the best extractive agents under the proposed conditions of this Table are typically n-hexane and carbon tetrachloride, the most effective extraction agent under industrial conditions may depend on the exact level and composition of impurities and the ability of the extractive agent to enable concomitant removal of the other impurities which may be present.

While certain aspects of the invention have been described in particular detail, a person in this art would understand that other embodiments and variations are covered.

What is claimed is:

1. A process for separating 1,1-difluoroethane from a first mixture comprising 1,1-difluoroethane and vinyl chloride, comprising:

contacting the first mixture with at least one extractive agent selected from the group consisting of hydrocarbons, alcohols, and chlorocarbons having a normal boiling point greater than about 10° C. and less than about 120° C. to form a second mixture, and separating 1,1-difluoroethane from the second mixture by extractively distilling the second mixture, thereby recovering 1,1-difluoroethane substantially free of vinyl chloride.

2. The process of claim 1 wherein the first mixture consists essentially of 1,1-difluoroethane, 1-chloro-1-fluoroethane, 1,1-dichloroethane, vinyl chloride, vinyl fluoride, hydrogen fluoride, and hydrogen chloride.

3. The process of claim 1 wherein the 1,1-difluoroethane resulting from said separating step contains less than about 50 ppm vinyl chloride.

4. The process of claim 1 wherein the extractive agent comprises at least one compound selected from the group consisting of normal pentane, cyclopentane, normal hexane, cyclohexane, normal heptane, chloromethane, dichloromethane (methylene chloride), trichloromethane (chloroform), carbon tetrachloride, chloroethane, 1,1-dichloroethane, 1,2-dichloroethane, 1,1,2-trichloroethane, methanol, ethanol, and propanol.

5. The process of claim 1 further comprising recycling at least a portion of the extractive agent obtained from the extractive distillation of said separation step for use in preparation of the second mixture of said contacting step.

6. The process of claim 1 wherein the extractive distillation is performed at a pressure from about 15 to 350 psia.

7. The process of claim 1 wherein the ratio of extractive agent to 1,1-difluoroethane is from about 1/1 to 10/1 by weight.

8. The process of claim 1 wherein the extractive distillation is performed using a reflux ratio of from about 1/1 to about 10/1 on a weight basis.

9. The process of claim 1 wherein said 1,1-difluoroethane and vinyl chloride of the first mixture are an azeotropic mixture.

* * * * *